United States Patent [19]

Ahlers et al.

[11] Patent Number: 5,759,826
[45] Date of Patent: Jun. 2, 1998

[54] PROCESS OF PREPARING AN ORGANIC ACID

[75] Inventors: Bernd Ahlers, Frankfurt am Main; Rudolf Bönsch, Nackenheim; Michael Eichelsbacher, Mainz; Jürgen Kuhn, Frankfurt am Main; Ulrich Sander, Friedrichsdorf, all of Germany; Jiri Pendl, Plzen, Czechoslovakia; Frantisek Hotek, Petrohrad, Czechoslovakia; Vaclav Cerny, Kaznejov, Czechoslovakia

[73] Assignee: Metallgesellschaft Aktiengesellschaft, Frankfurt am Main, Germany

[21] Appl. No.: 760,241

[22] Filed: Dec. 4, 1996

[30] Foreign Application Priority Data

Dec. 5, 1995 [DE] Germany .................. 195 45 303.4

[51] Int. Cl.⁶ .................. C12P 7/40; C12P 7/42
[52] U.S. Cl. .................. 435/136; 435/137; 435/138; 435/139; 435/142; 435/144; 435/146
[58] Field of Search .................. 435/136, 137, 435/138, 139, 142, 144, 146

Primary Examiner—Leon B. Lankford, Jr.
Attorney, Agent, or Firm—Herbert Dubno

[57] ABSTRACT

A process is disclosed for preparing an organic acid and/or its salts from a solution obtained through fermentation. In this process, a pure carbohydrate-containing raw material is used. The acid-containing solution prepared by means of fermentation is supplied to a cell separation, and the acid-containing permeate is supplied to a protein precipitation, where it is mixed with a silicon-containing precipitant at temperatures between 2° and 70° C. The solution thus obtained is supplied to a protein separation, and the acid-containing permeate is concentrated and then supplied to a single- or multi-stage crystallization or a granulation.

20 Claims, 2 Drawing Sheets

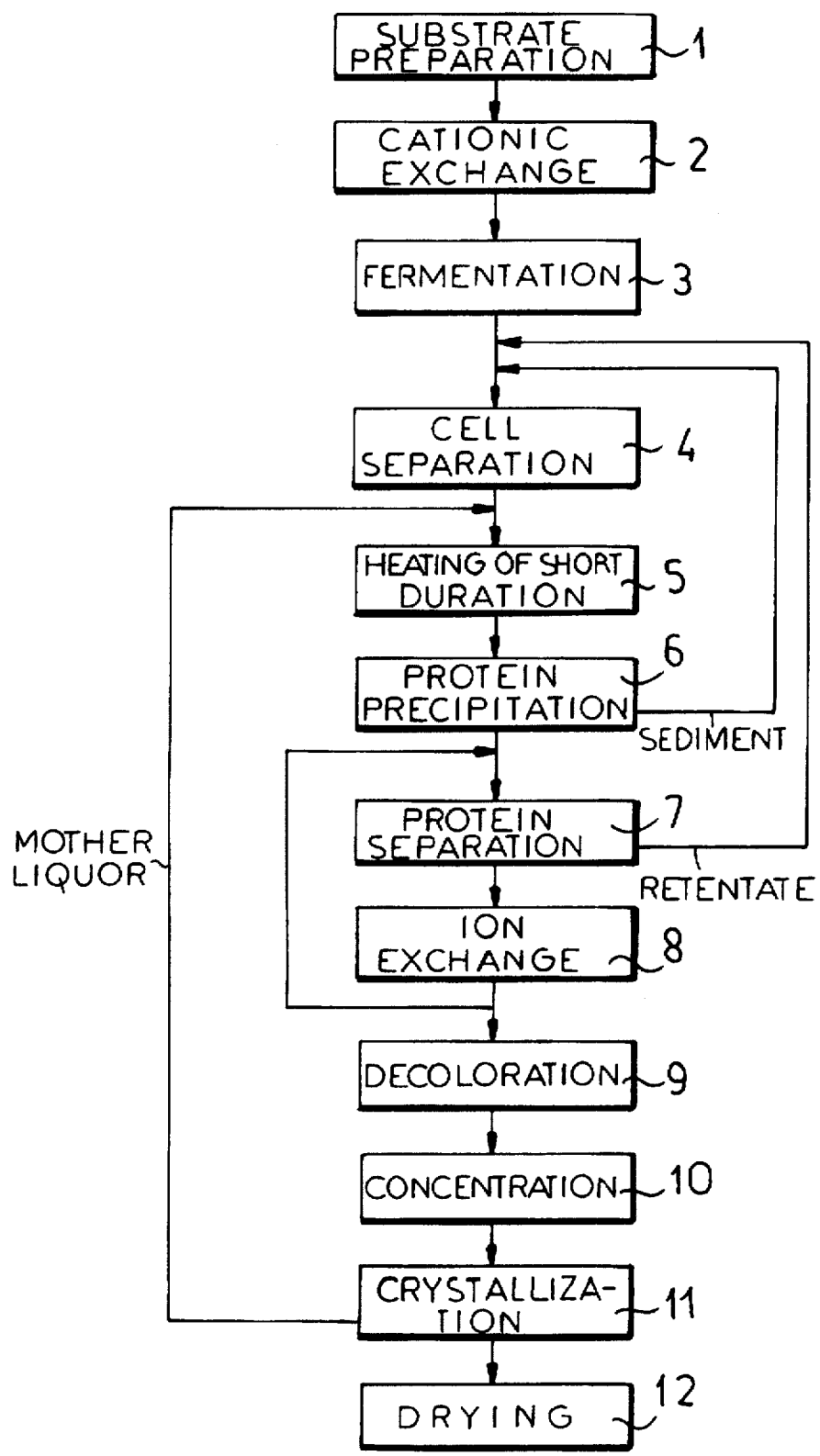

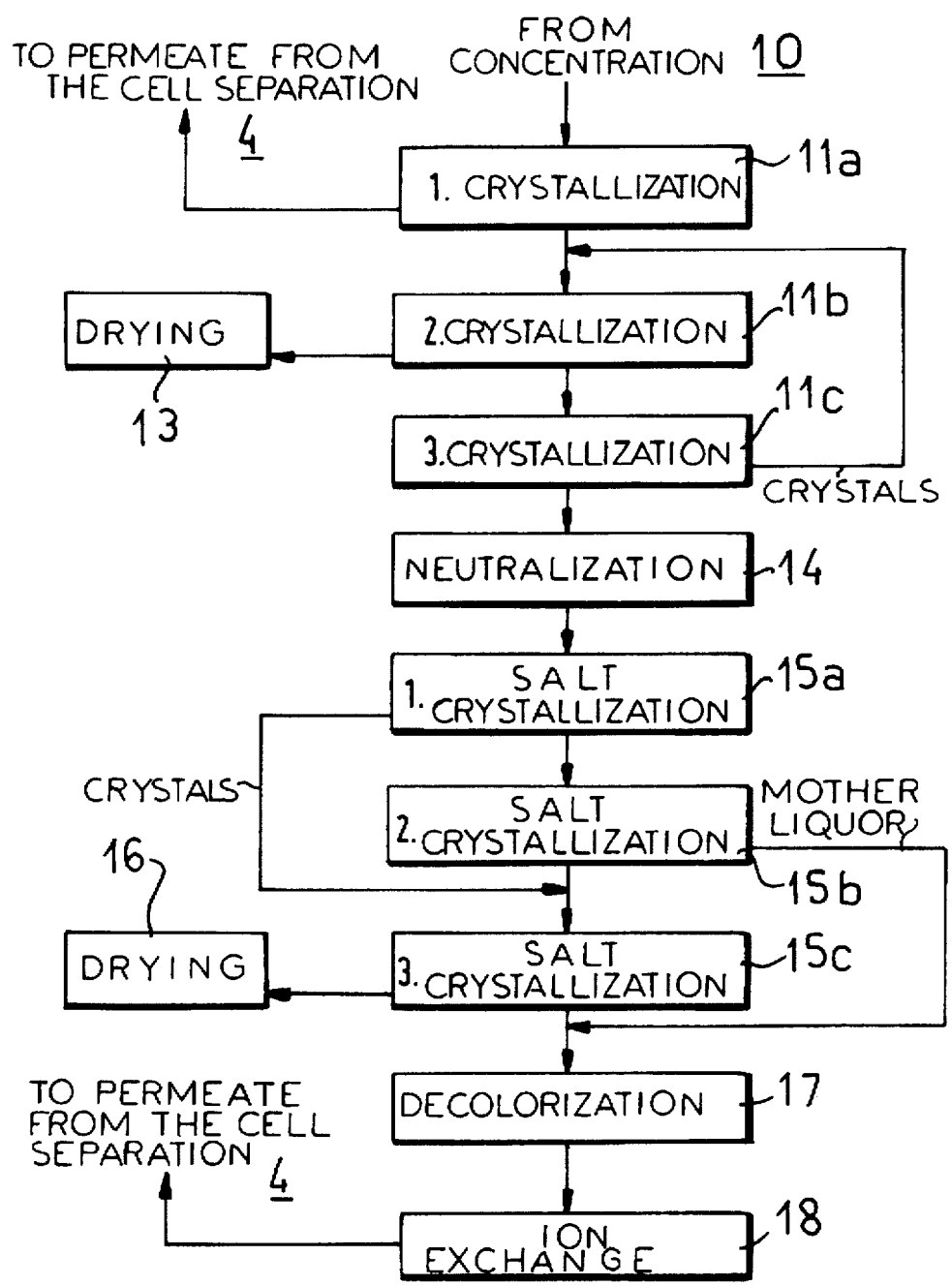

PROCESS OF PREPARING AN ORGANIC ACID

FIELD OF THE INVENTION

The present invention relates to a process of preparing an organic acid and/or its salts from a solution obtained through fermentation.

BACKGROUND OF THE INVENTION

Certain organic acids, such as citric acid, lactic acid and gluconic acid are largely prepared through fermentation. In the fermentation, a solution of the organic acid is produced from appropriate carbohydrate-containing raw materials in the presence of a microorganism, such as Aspergillus niger, for the preparation of citric acid. Subsequent to the fermentation, extensive processes for purifying this acid solution are performed, so as to achieve the purity required for a saleable product. Even a crystallization of the organic acid is only possible from a relatively pure acid solution, which has a low content of unreacted carbohydrates, proteins, amino acids and salts. For a particularly high purity of the product, as it is for instance required for an application in the food industry, and especially for a product in accordance with the specification of pharmaceutical quality, for instance according to the USP standard, which is described in the Pharmacopeia of the United States", XXII Edition, p. 315; even the crystallites must have a very high purity. This is only achieved through extensive purification process. The purification of the citric acid is, for instance, effected by precipitating the acid as calcium salt, separating the calcium citrate and reacting the calcium citrate produced with sulfuric acid. In the process, large amounts of sulfuric acid are consumed, and in addition contaminated calcium sulfate and a large amount of waste water are obtained. Even when using relatively pure carbohydrate-containing raw materials for the fermentation, it has so far been necessary to employ extensive purification processes. Such carbohydrate-containing raw materials include for instance glucose, dextrose, sucrose or purified and liquefied starch.

In U.S. Pat. No. 4,275,234 a process is described, where the organic acid is extracted from an aqueous solution by means of a solvent insoluble in water. In accordance with a process disclosed in EP-A 0 167 957 the organic acid is adsorbed on an ion exchanger and subsequently desorbed again. The DE-A-3 502 924 likewise describes a process where subsequent to a membrane filtration an adsorption of a non-ionogenic adsorber resin is performed. All the aforementioned processes have in common that there is a high loss of organic acid during the required desorption, and that a high effort is necessary to reasonably limit such loss. In addition, further purification steps are necessary to obtain organic acids of very high purity and corresponding color.

In EP-A-0 163 836 and EP-A-0 479 048 processes for granulating organic acids are described. In these processes, the solution to be granulated still has residual contents of unreacted carbohydrate-containing raw material in the range from 2 to 30 wt-%, with reference to the acid produced through fermentation. The granulation processes do not serve the further purification of the acid, but rather serve the conversion of the liquid acid to a solid, granular state that is favorable for transport purposes.

OBJECT OF THE INVENTION

It is the object of the present invention to provide an efficient and inexpensive process of preparing an organic acid and/or its salts from a solution obtained through fermentation, which acid satisfies the relatively high requirements as to purity that is up to pharmaceutical quality. Furthermore, the disadvantages of the purification process by means of precipitating the acid as calcium salt should be eliminated. There should, in particular, not be produced large amounts of waste, such as contaminated calcium sulfate and waste water.

SUMMARY OF THE INVENTION

This object is solved by a process where a pure, carbohydrate-containing raw material is used for making the substrate, where the acid-containing solution prepared by means of fermentation is supplied to a cell separation, where the acid-containing permeate from the cell separation is supplied to a protein precipitation, where it is mixed with a silicon-containing precipitant at temperatures between 2° and 70° C., where the solution thus obtained is supplied to a protein separation, and where the acid-containing permeate from the protein separation is concentrated and subsequently supplied to a single- or multi-stage crystallization or a granulation.

By "pure", carbohydrate-containing raw material it is meant that the degree of purity for instance of sugar is larger than about 95%. Useful carbohydrate-containing raw materials include for instance glucose, dextrose, sucrose or purified and liquefied starch. The cell separation is used above all for separating polymolecular impurities, in particular biomass such as mycelium, and coagulated proteins. The cell separation can for instance be effected through filtration or centrifugation. By means of the silicon-containing precipitant in particular dissolved proteins are precipitated as impurities, with a temperature of 2° to 70° C. ensuring an efficient precipitation and a safe operation.

The protein separation is for instance effected through filtration or centrifugation. Precipitated impurities and residual polymolecular impurities are separated. The solution is concentrated, for instance, through single- or multi-stage evaporation. From this concentrated acid solution a direct crystallization of the end product can be effected. The crystallization is carried out for instance as an evaporative crystallization or a cold crystallization, which can be effected continuously or discontinuously. As organic acids $C_2$ to $C_6$ hydroxy-substituted alkane carboxylic acids containing one or more carboxy groups, for instance citric acid, lactic acid, gluconic acid, malic acid and tartaric acid can be prepared by means of the process in accordance with the invention. The acids thus prepared have a surprisingly high purity that are up to the purity demands of good quality. It is a particular advantage of the inventive process that in this precipitation by means of a silicon-containing precipitant only impurities are precipitated. In the precipitation method in accordance with the prior art, however, the entire acid solution is precipitated, for instance, as a calcium salt, and very large amounts of waste, for instance calcium sulfate, are produced. In addition, in the processes employing the precipitation as calcium salt there are also produced very large amounts of waste water, which are not produced in the process in accordance with the invention. Therefore, the process in accordance with the invention is clearly superior to the process in accordance with the prior art, both from an economical and from an ecological point of view.

In accordance with a further aspect of the invention pure glucose, sucrose or pure, enzymatically liquefied starch of raffinate stage 1 with a content of higher sugars below 5% is used as pure, carbohydrate-containing raw material for the preparation of a substrate. In this connection, it is particularly advantageous when glucose and sucrose only have a content of higher sugars below 1 to 2%.

In accordance with a further aspect of the invention, the pure carbohydrate-containing raw material for making the substrate is supplied to a cation exchange prior to its fermentation. With this procedure, metal cations such as iron and magnesium and in particular manganese are separated, which would otherwise disturb the process of the acid production.

In accordance with a further aspect of the invention the cell separation is carried out by means of filtration. By means of this process, which can relatively easily be realized in technical terms and is thus inexpensive, the content of polymolecular impurities in the solution can be decreased considerably. There can, for instance, be used a band filter, a vacuum-drum filter or a membrane filter. The membrane filtration can be used for solutions having a temperature below about 50%. By means of this separation, the polymolecular impurities are separated to a content below about 1 g/l.

In accordance with a further aspect of the invention the cell separation is carried out by means of a membrane filtration with a filter having a pore size of 0.1 to 5 µm. The advantage of this pore size consists in a surprisingly high permeate efficiency of the filter.

In accordance with a further aspect of the invention the permeate from the cell separation is heated prior to the protein precipitation for a period of 0.5 to 10 min. to a temperature above 70° C., preferably 80° to 100° C. As a result of this heat treatment, the proteins to be precipitated are at least partly coagulated, and active proteases of the mycelium are deactivated.

In accordance with a further aspect of the invention, after a settling time of 30 to 300 min. the sediment from the protein precipitation is returned to the acid-containing solution before the cell separation, and the supernatant from the protein precipitation is supplied to the protein separation. Due to the recirculation of the sediment from the protein precipitation, the subsequent cell separation is improved.

In accordance with a further aspect of the invention the protein separation is carried out by means of a membrane filtration. The membrane filtration can, for instance, be carried out as a cross-flow process by means of membranes made of a ceramic material.

In accordance with a further aspect of the invention the protein separation is carried out by means of a membrane filtration, which consists of combination of a microfiltration with a filter having a pore size of 0.05 to 5 µm and an ultrafiltration with a particle exclusion limit to below 5000 Daltons. By means of this procedure, the polymolecular impurities are advantageously separated to a content below about 2 mg/l.

In accordance with a further aspect of the invention the protein separation is carried out by means of a membrane filtration, which consists of a combination of a microfiltration with a filter having a pore size of 0.05 to 5 µm, an ultrafiltration with a particle exclusion limit: to below 2000 Daltons, and a nanofiltration with a particle exclusion limit to below 200 Daltons. By means of this procedure, the polymolecular impurities are advantageously separated to a content below about 1 mg/l.

In accordance with a further aspect of the invention the residue from the protein separation is returned to the acid-containing solution before the cell separation, or is washed out with fully de-ionized water, and the citric acid thus eluted is subjected to an ion exchange, a membrane-electrodialysis or a precipitation as calcium salt, and is then returned to the acid containing solution before the cell separation, or supplied to a further use. By means of this procedure, the remaining acid can advantageously be separated in a high concentration. The concentrate of the acid thus obtained can be crystallized or granulated for a further use. The residue from the protein separation, which contains little or no citric acid, can be combined with the washed mycelium from the cell separation.

In accordance with a further aspect of the invention the permeate from the protein separation is subjected to an ion exchange and/or a decoloration. As ion exchangers there can, for instance, be used cation exchangers and slightly basic anion exchangers on the basis of a polymer or a gel. In this way, residual, in particular low-molecular salts and amino acids, are advantageously separated. As a result, the residual content of impurities lies in the range from 0.2 to 2 mg/l of free aminoacid nitrogen. The decoloration can advantageously be effected by means of a treatment with activated carbon, where this treatment is, for instance, carried out before concentrating the solution. The treatment with activated carbon can, for instance, be effected in a fixed bed.

In accordance with a further aspect of the invention the ion exchanger consists of a highly acid cation exchanger and/or a slightly basic anion exchanger, and the anion exchanger first of all elutes the organic acid such as citric acid with a 5 to 10% hydrochloric acid solution and is then regenerated with a 3 to 7% sodium hydroxide solution, or the anion exchanger is regenerated with an ammonia solution. On the cation exchanger, a large part of the amino acids contained in the solution is retained in addition to the cations, and the anion exchanger retains the anions and a further part of amino acids. The sodium hydroxide solution for the regeneration is preferably used in a concentration of about 5%. A 2 to 3% ammonia solution has turned out to be particularly useful for the regeneration of the anion exchanger.

In accordance with a further aspect of the invention, the crystallization is effected in three stages;, where the crystallites from the first crystallization stage are dissolved in fully de-ionized water and are supplied to a second crystallization stage, where the mother liquor from the second crystallization stage, is supplied to the third crystallization stage, where the crystallites from the third crystallization stage are dissolved in fully deionized water and are returned to the second crystallization stage, and where the mother liquor of the third crystallization stage, is supplied to a further use. The crystallites from the second crystallization stage can be marketed as crystals or acid granules after having been dried or spray dried. This acid has a purity up to pharmaceutical quality.

In accordance with a further aspect of the invention, the mother liquor from the crystallization or the third crystallization stage of the acid is neutralized, and the salt of the organic acid is supplied to a single- or multi-stage salt crystallization. The neutralization can for instance be effected with sodium hydroxide solution, whereby a sodium salt of the organic acid is formed.

In accordance with a further aspect of the invention the salt crystallization is effected in three stages, where the mother liquor from the first salt crystallization stage is supplied to a second salt crystallization stage, where the crystallites of the second salt crystallization stage are combined with those of the first salt crystallization stage, where the combined crystallites from the first and the second salt crystallization stage are dissolved in fully de-ionized water and are supplied to a third salt crystallization stage, and where the mother liquor from the third salt crystallization stage is combined with the mother liquor from the second salt crystallization stage and is supplied to a further use. The crystallites from the third salt crystallization stage can be marketed as crystals or acid granules after having been dried or spray dried. This acid has a purity up to pharmaceutical quality.

In accordance with a further aspect of the invention the mother liquor from the third crystallization stage or the mother liquor from the salt crystallization or the combined mother liquor from the second and the third salt crystallization steps are supplied to an ion exchange and/or a decoloration. For the ion exchange, a cation exchanger and an anion exchanger or a combination of a cation exchanger and an anion exchanger can, for instance, be used. In this way, low-molecular salts and amino acids are advantageously separated. The decoloration can advantageously be effected by means of a treatment with activated carbon, for instance in a fixed bed.

In accordance with a further aspect of the invention, the crystallites from the crystallization or the second crystallization stage and/or the salt crystallization or the third salt crystallization stage are suspended in a liquid and granulated subsequently. The acid crystals cart, for instance, be suspended in fully de-ionized water, and be converted to a solid product by means of spray granulation. By means of this procedure, acid granules having improved solid properties as compared to the original crystallites can advantageously be produced.

In accordance with a further aspect of the invention, the mother liquor from the crystallization or the first crystallization stage and/or the salt crystallization or the third salt crystallization stage is subjected to an ion exchange, a membrane-electrodialysis or a precipitation as calcium salt, and is then returned to the permeate from the cell separation or supplied to a further use. By means of this procedure the remaining acid can advantageously be separated from impurities in a high concentration. The acid concentrate thus obtained can be crystallized or granulated for a further use. For instance, the mother liquor can advantageously be converted to a solid product by means of spray granulation. The acid granules thus obtained can be employed as a solid commercial product for instance in process technology, but also in food technology.

In accordance with a further aspect of the invention a 25 to 35% $SiO_2$ solution, where $SiO_2$ has a specific surface larger than 100 m²/g, is used as silicon-containing precipitant. In the 25 to 35% $SiO_2$ solution, where $SiO_2$ has a specific surface of at least 100 m²/g, is very suitable, where the $SiO_2$ should preferably have a specific surface of at least 500 m²/g.

In accordance with a further aspect of the invention, the inventive process for preparing citric acid as the organic acid is used. The preparation of citric acid by means of the inventive process is preferred, as by means of the protein precipitation with the silicon-containing precipitant, at a pH of about 1.5 to 2.0, a relatively large amount of proteins and residual polymolecular impurities is precipitated. In this way, a relatively pure citric acid without precipitation of this acid as calcium salt can advantageously be prepared.

BRIEF DESCRIPTION OF THE DRAWING

The above and other objects, features, and advantages will become more readily apparent from the following description, reference being made to the accompanying drawing in which:

FIG. 1 is a flow diagram which shows the course of the inventive process with reference to the preparation of citric acid of food quality;

FIG. 2 is a flow diagram shows the course of the inventive process with reference to the preparation of citric acid of pharmaceutical quality.

DETAILED DESCRIPTIVE OF THE DRAWINGS

EXAMPLE 1

Preparation of citric acid from a fermentatively obtained citric acid solution as a crystalline or granular commercial product of food quality (see FIG. 1).

First of all, the substrate is prepared (1). For this purpose, highly purified, enzymatically liquefied starch or glucose syrup is diluted, or crystalline glucose or sucrose or raffinate stage 1 is dissolved in a corresponding concentration. The sugar or starch solution thus prepared is passed over a cation exchanger (2) and subsequently supplied to a continuous pasteurization. The salts required for fermentation are mixed in a separate mixing vessel. These salts are sources at assimilable nitrogen, phosphate and magnesium. Sources of assimilable nitrogen include ammonium nitrate, ammonium sulfate and ammonium chloride. A good phosphate source is $KH_2PH_4$. A good magnesium source is $MgSO_4 \cdot 7H_2O$. The medium from the substrate preparation (1) is supplied to a fermentation (3). In a fermenter, the medium is inoculated with spores of the fungus Aspergillus niger. After the fermentation (3) the solution is supplied to a cell separation (4), where the cells are separated from the fermentation solution, for instance by means of a vacuum band filter. The preparation of the citric acid solution is effected discontinuously with a batch volume of at least 50 m³, preferably 150 to 200 m³, and an amount of citric acid of 180 to 200 kg citric acid monohydrate/m³ or 27 to 40 t citric acid monohydrate/batch. The permeate from the cell separation (4) contains about 10 to 25% citric acid in dissolved form and in addition to other dissolved organic and inorganic constituents a minor amount of undissolved residual biomass. The acid-containing permeate is heated for a period of 2 to 3 min to a temperature of about 75° C. (5) and is then supplied to a protein precipitation (6). In the batch operation, colloidally dissolved proteins and other organic substances are precipitated by adding 1 to 10 l/m³ of a 30% $SiO_2$ solution, where $SiO_2$ has a specific surface of at least 500 m²/g. The temperature during the protein precipitation (6) is about 50° C., and the pH of the solution lie in the range from 1.5 to 2.0. After a relatively short settling time of 1 to 2 hours, the sediment is returned to the fermentation solution before the cell separation (4), and the supernatant is supplied to a protein separation (7) by means of a membrane filtration. The membrane filtration is performed continuously with a volume flow depending on the respective type and size of the filtration unit. It can, for instance, lie in a range from 5 to 15 m³/h. The membrane filtration is performed by means of a method consisting of a combination of a microfiltration with a filter having a pore size of 0.05 to 5 μm and an ultrafiltration with a particle exclusion limit to below 5000 Daltons, preferably 2000 Daltons. In addition, a nanofiltration with a particle exclusion limit to below 200 Daltons can be effected. During the protein separation (7) the residue is concentrated and added to the fermentation solution before the cell separation (4), or from the residue of the protein separation (7) adhering citric acid is eluted by means of de-ionized water and returned to the process, while the residue now almost completely free of citric acid is discharged from the process. The residue includes cells as undissolved substances, which were not precipitated by means of the vacuum band filter, as well as precipitated proteins and other organic constituents with a particle size of at least 5000 to 2000 or 200 Daltons. The permeate, a clear solution, contains dissolved citric acid as well as dissolved organic and inorganic constituents. For the further processing the permeate from the protein separation (7) is continuously passed over an ion exchanger (8). The ion exchanger (8) consists, for instance, of two stages including a highly acid cation exchanger and a slightly basic anion exchanger. On the cation exchanger a large part of the amino acids contained in the solution are retained in addition to the cations. The anion exchanger retains the anions and an additional part of the amino acids. A breakthrough of substances is measured by means of a conductivity meter or a pH meter. If necessary, the system is switched over to another pair of ion exchangers, so that a relatively safe separation of disturbing cations, anions and amino acids can be ensured. Citric acid is eluted by the anion exchanger with a 5 to 10% hydrochloric acid solution, and the anion exchanger is subsequently regenerated with an about 5% sodium hydroxide solution or with an ammonia solution, preferably a 2 to 3% ammonia solution. During the regeneration with an ammonia solution ammonium citrate is formed, which is decomposed upon heating, which again leads to the formation of citric acid. This citric acid can be returned to the process. It can either be returned to the solution after the cell separation (4), or it can be returned to the solution before the ultrafiltration of the protein separation (7). The ammonia can be recovered by means of washing as a stock solution having a purity of up to 20%. It is likewise possible to use the regenerated ion exchanger for purifying the mother liquor, which is formed in the course of the further process. This is particularly advantageous in the case of relatively high concentrations of residual sugar and free amino acids in the mother liquor. These relatively high concentrations can, for instance, be achieved when the mother liquor is circulated. The citric acid solution thus regenerated contains a certain amount of colorants. The same are continuously removed from the solution in a decoloration (9) in a fixed bed of activated carbon. The decolorized solution is supplied to a concentration (10), where the acid solution is continuously evaporated by means of a multi-stage process to a concentration of 60 to 70%, preferably about 67%. The concentrated citric acid is supplied to a crystallization (11) or concentrated and granulated. The mother liquor of the crystallization (11) is returned to the permeate of the cell separation (4). Before doing so, the mother liquor can be regenerated by means of an ion exchanger, and electrodialysis or a precipitation of the acid as a citrate. The citric acid crystallites produced in this first crystallization already have a purity corresponding to food quality. Upon drying (12), these crystallites can be marketed as an end product.

EXAMPLE 2

Preparation of citric acid from a fermentatively obtained citric acid solution as a crystalline or granular commercial product of pharmaceutical quality (see FIG. 2).

The crystallites from the first crystallization stage (11a) obtained by the process in accordance with Example 1, are dissolved in fully de-ionized water and supplied to a second crystallization stage (11b). Upon drying (13), they can be marketed. These crystallites already have pharmaceutical quality according to the USP and BP standards. From the mother liquor of the second crystallization stage (11b) further crystals are recovered in a third crystallization stage (11c), which crystals are dissolved in fully deionized water and are returned to the second crystallization stage (11b). The mother liquor of the third crystallization stage (11c), which in addition to citric acid also contains the residual impurities left in the process in a concentrated form, is further used for recovering sodium citrate, granulated or regenerated and again supplied to the protein precipitation (6). The regeneration can be effected by means of an ion exchanger, an electrodialysis or a precipitation of the acid as calcium citrate. The crystallization is effected continuously or discontinuously.

EXAMPLE 3

Preparation of sodium citrate from the mother liquor of a crystallization of fermentatively obtained citric acid solution as a crystalline or granular commercial product of pharmaceutical quality (see FIG. 2).

The mother liquor from the third crystallization stage (11c) in accordance with example 2 is supplied to a neutralization (14). In doing so, the acid-containing mother liquor is neutralized by adding sodium hydroxide solution and supplied to a first salt crystallization stage (15a), where crystallites are formed from sodium citrate. From the mother liquor produced in the process, further crystallites are recovered in a second salt crystallization stage (15b), which crystallites are combined with the first salt crystallization (15a). The combined crystallites are dissolved in fully deionized water and supplied to a third salt crystallization stage (15c). The mother liquor from the third salt crystallization stage 15(c) is combined with the mother liquor from the second salt crystallization stage 15(b). The crystallites from the third salt crystallization stage (15c) have pharmaceutical quality according to the USP and EP standards. They are supplied to drying (16) or spray drying and used as crystalline or granular commercial product. The recovery of the sodium citrate is operated continuously. The mother liquors from the second (15b) and the third salt crystallization stage (15c) contain citric acid and in addition residual impurities from the process. From these mother liquors the remaining citric acid is recovered and returned to the regeneration process. For the recovery of the remaining citric acid the mother liquors are supplied to a decoloration (17) on a fixed bed of activated carbon and subsequently to a cation exchange (18), in order to obtain free citric acid. The regeneration can also be effected through a further ion exchange, a membrane-electrodialysis or a precipitation of the acid as calcium citrate. This citric acid solution is returned to the process to the permeate from the cell separation (4). The decoloration (17) and the cation exchange (18) are effected continuously.

By means of the process described in example 3 a total yield of citric acid of about 95% is achieved, where about 70 to 90% are obtained in the first process stage in accordance with example 2, and another about 20 to 30% in the second process stage in accordance with example 3.

What is claimed is:

1. A process for preparing an organic acid or a salt thereof, which comprises the following steps:
   (a) preparing a pure, carbohydrate raw material substrate by dissolving a pure carbohydrate in water to form an aqueous solution;
   (b) inoculating said substrate with a microorganism capable of fermenting the substrate and adding a salt required to carry out fermentation to the substrate to ferment the substrate thereby obtaining a permeate containing the organic acid in solution, cells of the microorganism, and colloidally dissolved proteins;

(c) separating the cells of the microorganism from the permeate containing the organic acid in solution and the colloidally dissolved proteins;

(d) precipitating as a sediment a portion of the colloidally dissolved proteins in the permeate containing the organic acid in solution and the colloidally dissolved proteins by employing a silicon-containing precipitant at a temperature of 2° to 70° C. while the permeate containing the organic acid in solution and the remainder of the colloidally dissolved proteins remain as a supernatant;

(e) separating the remaining proteins in the supernatant formed during step (d) from the permeate containing the organic acid in solution to form a protein residue and the organic acid in solution;

(f) concentrating the organic acid in solution; and (g) either crystallizing or granulating the organic acid to obtain the organic acid and a mother liquor; and (h) in the case where the desired product is the salt of an organic acid, reacting the organic acid with a base capable of forming a salt of the organic acid.

2. The process defined in claim 1 wherein according to step (a) the pure carbohydrate is glucose, sucrose or enzymatically liquefied starch of raffinate stage 1 each with a content of higher sugars below 5%.

3. The process defined in claim 1 wherein prior to step (b) the pure, carbohydrate raw material substrate is passed through a cationic exchange resin to remove metal cations from said substrate.

4. The process defined in claim 1 wherein according to step (c) the cell separation is performed by filtration.

5. The process defined in claim 4 wherein the cell separation is performed by means of a microfiltration with a filter having a pore size of 0.1 to 5 μm.

6. The process defined in claim 1 wherein prior to step (d) the permeate containing the organic acid in solution and the colloidally dissolved proteins is heated for a period of 0.5 to 10 minutes to a temperature above 70° C.

7. The process defined in claim 1 wherein following step (d) after a settling time of 30 to 300 minutes the sediment from the protein precipitation is returned prior to step (c) to the permeate containing the organic acid in solution, cells of the microorganism, and colloidally dissolved proteins.

8. The process defined in claim 1 wherein according to step (e) the protein separation is performed using a membrane filtration.

9. The process defined in claim 8 wherein the membrane filtration consists of a combination of microfiltration with a filter having a pore size of 0.5 to 5 μm and an ultrafiltration with a particle exclusion limit to below 5000 Daltons.

10. The process defined in claim 8 wherein the membrane filtration consists of a combination of microfiltration with a filter having a pore size of 0.5 to 5 μm and an ultrafiltration with a particle exclusion limit to below 2000 Daltons, and a nanofiltration with a particle exclusion limit to below 200 Daltons.

11. The process defined in claim 1 wherein the protein residue obtained according to step (e) is returned prior to step (c) to the permeate containing the organic acid in solution, cells of the microorganism, and colloidally dissolved proteins, or is washed out with deionized water, and any of the organic acid thus eluted from said protein residue is subjected to an ion exchange, a membrane-electrodialysis, or a precipitation to form the calcium salt of the organic acid which then is returned prior to step (c) to the permeate containing the organic acid in solution, cells of the microorganism, and colloidally dissolved proteins, while the protein residue is discharged from the process.

12. The process defined in claim 1 wherein following step (e) the organic acid in solution is passed through at least one ion exchange resin to remove amino acid impurities and through activated charcoal to remove colorants.

13. The process defined in claim 12 wherein the at least one ion exchange resin includes a highly acid cation exchange resin and a weakly basic anion exchange resin, and wherein the anion exchange resin first of all eludes the organic acid with a 5 to 10% hydrochloric acid solution and is then regenerated with a 3 to 7% sodium hydroxide solution, or wherein the anion exchange resin is regenerated with an ammonia solution.

14. The process defined in claim 1 wherein according to step (g) the crystallization is carried out in three stages, where crystallites from the first crystallization stage are dissolved in deionized water and are supplied to a second crystallization stage, wherein mother liquor from the second crystallization stage is supplied to a third crystallization stage, wherein the crystallites from the third crystallization stage are dissolved in deionized water and are returned to the second crystallization stage.

15. The process defined in claim 1 wherein according to step (g) the mother liquor obtained after crystallization of the organic acid is neutralized to form a salt of the organic acid and the salt of the organic acid is supplied to a single- or multi-stage salt crystallization.

16. The process defined in claim 15, wherein the salt crystallization is effected in three stages: where mother liquor from a first salt crystallization stage is supplied to a second salt crystallization stage, where crystallites of the second salt crystallization stage are combined with crystallites of the first salt crystallization stage, where the combined crystallites from the first and the second crystallization stages are dissolved in deionized water and are supplied to a third salt crystallization stage, and where mother liquor from the third salt crystallization stage is combined with the mother liquor from the second salt crystallization stage.

17. The process defined in claim 16 wherein the mother liquor from the third crystallization stage or the mother liquor from the salt crystallization stage or the combined mother liquors from the second and third salt crystallization stages are passed through at least one ion exchange resin to remove amino acid impurities and through activated charcoal to remove colorants.

18. The process defined in claim 17 wherein the crystallites from the crystallization or the second crystallization stage or the salt crystallization or the third salt crystallization stage are suspended in a liquid and are then granulated.

19. The process defined in claim 15 wherein the mother liquor from the crystallization, the first crystallization stage, the salt crystallization or the third salt crystallization stage is subjected to an ion exchange, a membrane electrodialysis or a precipitation to form the calcium salt of the organic acid, and is then returned prior to step (c) to the permeate containing the organic acid in solution, cells of the microorganism, and colloidally dissolved proteins, while the protein residue is discharged from the process.

20. The process defined in claim 1 wherein according to step (d) as the silicon-containing precipitant, a 25 to 35% $SiO_2$ colloidal solution, where the $SiO_2$ has a specific surface larger than 100 $m^2/g$ is used.

\* \* \* \* \*